United States Patent [19]

Reynolds

[11] Patent Number: 4,861,335
[45] Date of Patent: Aug. 29, 1989

[54] SYRINGE

[75] Inventor: David L. Reynolds, Montreal, Canada

[73] Assignee: Duoject Medical Systems Inc., Montreal, Canada

[21] Appl. No.: 18,934

[22] Filed: Feb. 25, 1987

Related U.S. Application Data

[63] Continuation-in-part of Ser. No. 759,432, Jul. 26, 1985, abandoned.

[51] Int. Cl.⁴ .............................................. A61M 3/00
[52] U.S. Cl. ...................................... 604/88; 604/191
[58] Field of Search ...................... 604/87, 88, 82, 56, 604/89–92, 191, 413, 414, 416; 222/80

[56] References Cited

U.S. PATENT DOCUMENTS

| | | | |
|---|---|---|---|
| 2,684,068 | 7/1954 | Orens | 604/88 |
| 3,477,432 | 11/1969 | Shaw | 604/91 |
| 3,489,147 | 1/1970 | Shaw | 604/88 |
| 3,636,950 | 1/1972 | Gomez et al. | 604/88 |
| 3,724,460 | 4/1973 | Gomez et al. | 604/88 |
| 4,171,698 | 10/1979 | Genese | 604/88 |
| 4,405,317 | 9/1983 | Case | 604/90 |
| 4,581,016 | 4/1986 | Gettig | 604/92 |

Primary Examiner—Stephen C. Pellegrino
Assistant Examiner—Ralph Lewis
Attorney, Agent, or Firm—Ridout & Maybee

[57] ABSTRACT

A syringe provides for the isolated storage of two components of a medicament until immediately prior to use of the syringe. One liquid component is stored in a collapsible chamber of a sealed capsule within a hollow plunger stem of the syringe, and the other component beneath the head of the plunger. A double headed needle arrangement between the head and stem of the plunger is caused to penetrate the plunger head and the capsule when the syringe is to be used so that the plunger may be drawn back to exhaust the contents of the capsule chamber into admixture with the component stored beneath the head of the plunger. Communication through the double headed needle arrangement is then interrupted before the plunger is used to eject the syringe contents through an external needle fitted to the syringe.

15 Claims, 6 Drawing Sheets

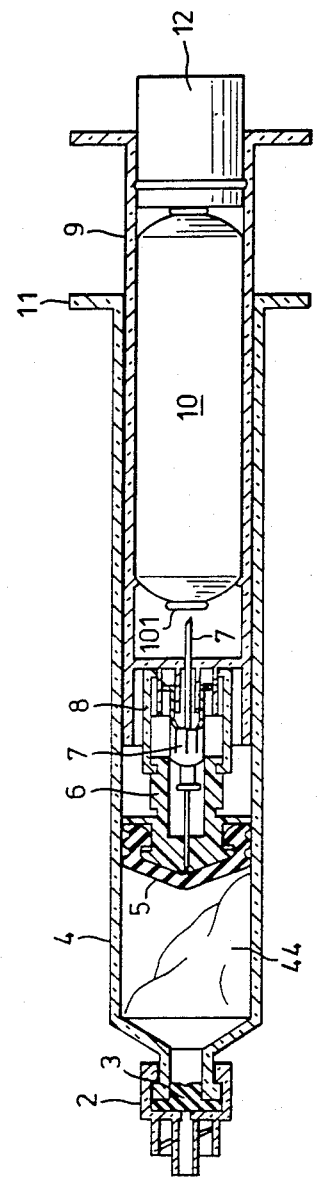
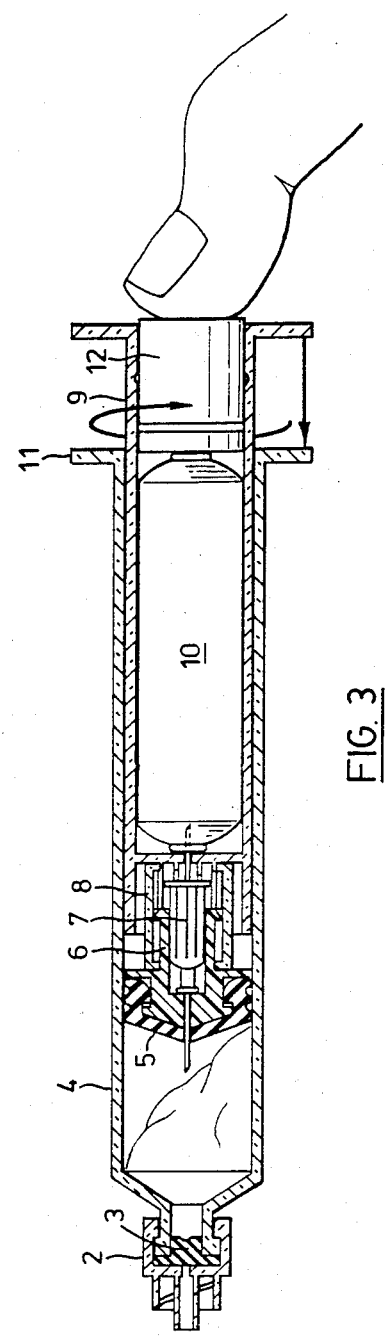
FIG. 2
FIG. 3

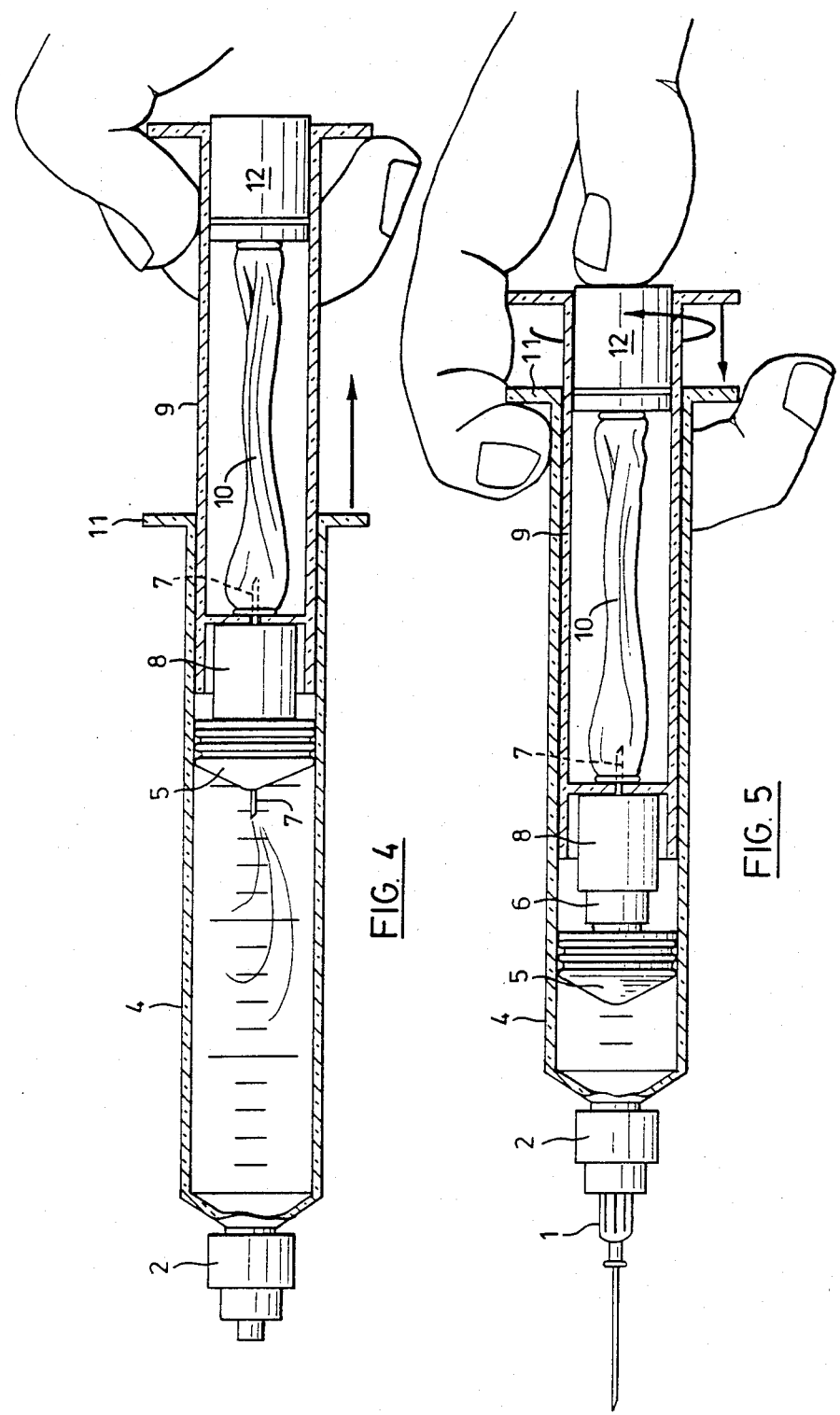

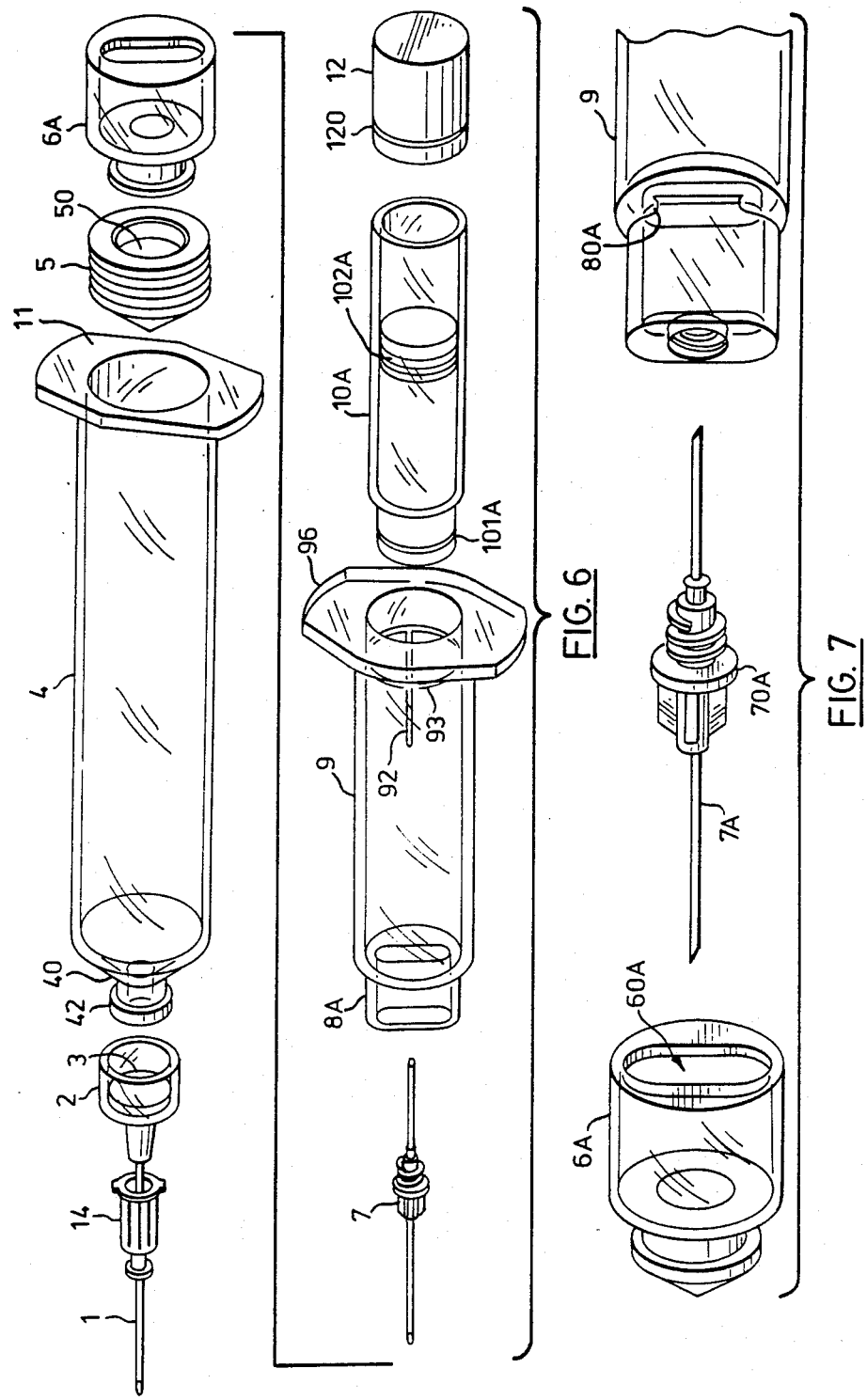

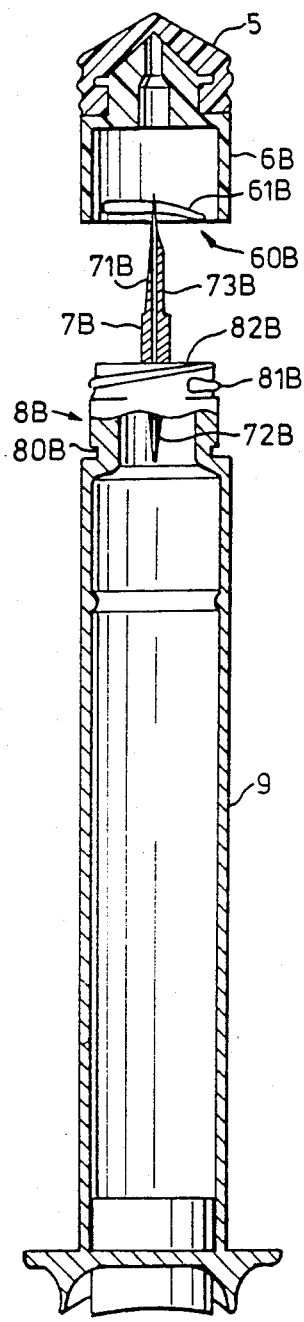
FIG. 8
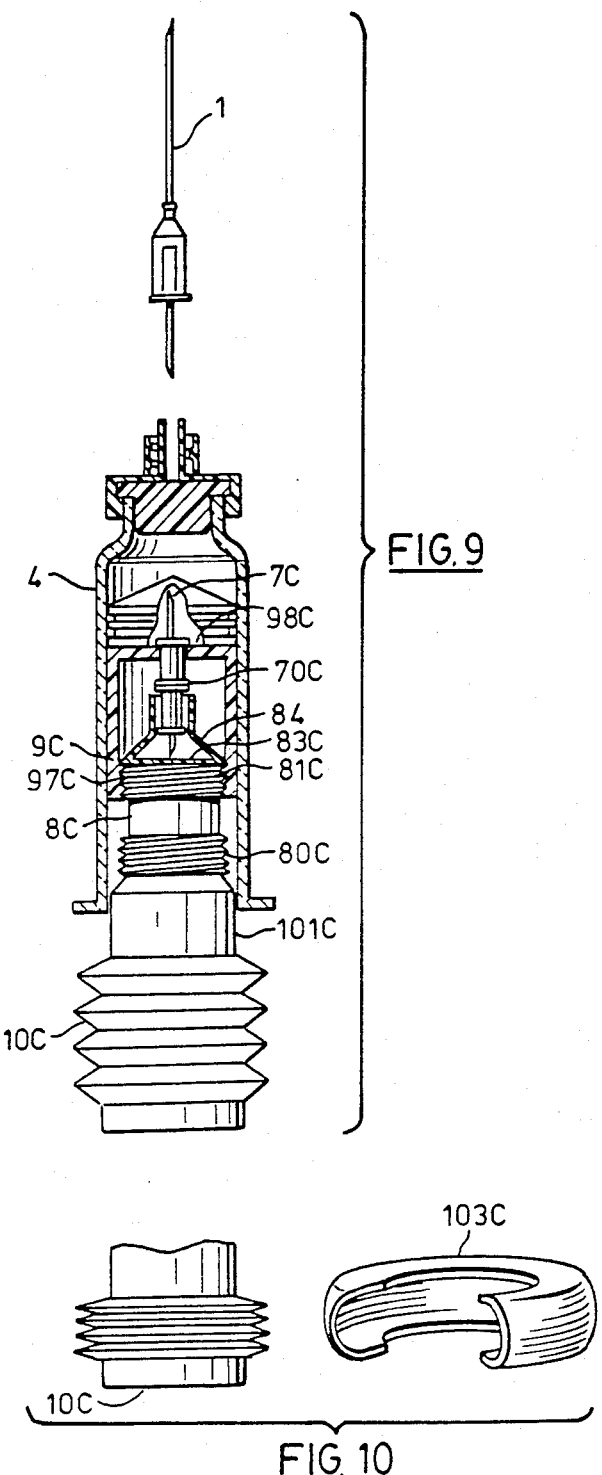
FIG. 9
FIG. 10

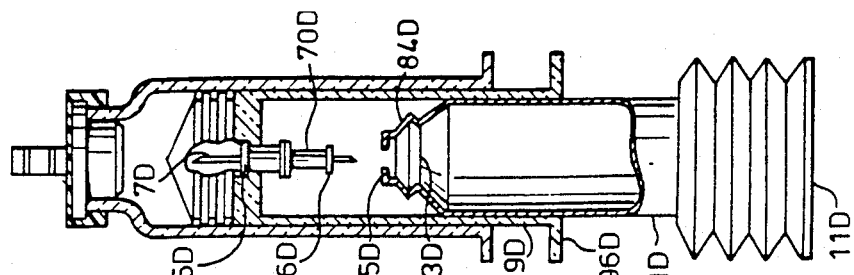
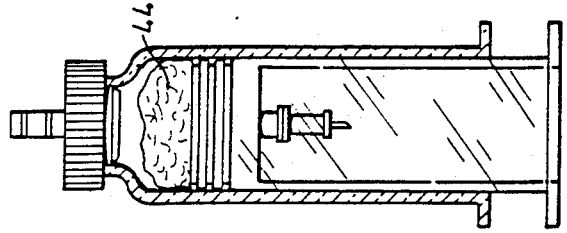
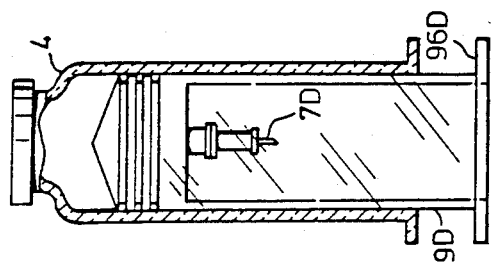
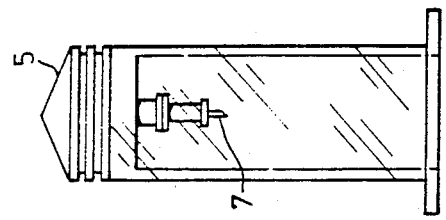
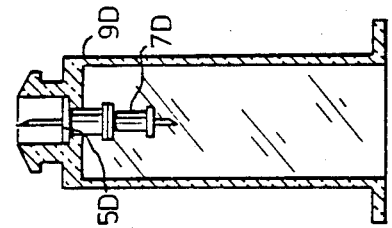
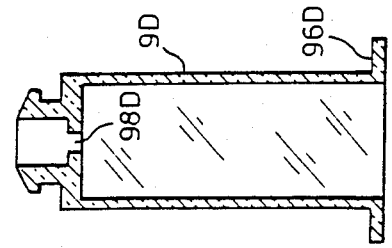

SYRINGE

REFERENCE TO RELATED APPLICATION

This application is a continuation-in-part of my copending application Ser. No. 759,432, filed July 26, 1985, now abandoned.

This invention relates to hypodermic syringes of the type providing for the isolated storage of two separate components until immediately prior to use of the syringe.

BACKGROUND OF THE INVENTION

In the case of many pharmaceuticals, injectable solutions or suspensions formed from them have insufficient stability to allow for prolonged storage prior to use, although the product prior to solution, dilution or suspension may have adequate stability. Preparation of the injectable product at the time of use from two components presents various problems in that it is time consuming, requires additional apparatus, and is prone to error and loss of sterility; there is therefore a demand for disposable prefilled syringe systems permitting the components to be readily mixed within the system at the time of use, in predetermined proportions and with the maintenance of sterile conditions.

A number of such systems have been proposed, but to the best of applicant's knowledge, none has received widespread acceptance. In a first type of system, the plunger of a first syringe, the barrel of which contains a first component of an injectable medicament and is provided with means for mounting a hypodermic needle, is formed by a second concentric syringe, the barrel of which contains a fluid second component of the medicament, and which is provided, in place of a hypodermic needle with some form of non-return valve. In use, a plunger of the second syringe is pressed into the barrel of the latter to expel its contents through the non-return valve into the first syringe, whereafter the second syringe may be used as the plunger of the first syringe to expel the now mixed contents of the latter through a hypodermic needle attached to the first barrel. The weak point of this arrangement is the non-return valve, which must positively separate the two components during storage, yet open readily during use. In practice, it is desirable that the component be positively sealed apart during storage, and any system which relies solely on a pressure differential operated non-return valve cannot provide such a positive seal. Examples of such systems are discussed for example in U.S. Pat. Nos. 3,659,749 (Schwartz), 3,678,931 and 3,682,174 (Cohen), 3,685,514 (Cheney), 4,405,317 (Case) and 4,464,174 (Ennis), and the multiplicity of valve designs disclosed and discussed in these patents is illustrative that the existence of problems associated with design of a suitable non-return valve is well appreciated in the art.

In another type of system, a single barrel and plunger are employed, and the components are separated within the barrel by a sliding seal system having portions relatively movable under the influence of differential pressures such that a needle incorporated in the sliding seal systems ruptures the seal provided by the system so as to permit the plunger to force a liquid component through the needle into admixture with the other component prior to injection. Very careful design is obviously necessary to provide the correct differential pressures and degrees of flexibility and frictional engagement between the parts if correct operation is to be assured, and the overall length of the system is comparatively large. Separation between the components relies on a sliding plug or plugs. Examples of such systems are shown in U.S. Pat. Nos. 4,055,177 (Cohen) and 4,059,109 (Tischlinger). In both the above discussed types of syringe, the entire contents of both components must be mixed before use of the syringe.

U.S. Pat. No. 4,060,082 (Lindberg et al) shows a system which consists in effect of two syringes connected in tandem by a collapsible sleeve. By collapsing the sleeve, the contents of a second of the syringes may be injected through a soft rubber head of a first of the syringes. The second syringe is then removed, and a plunger shaft is attached to the plunger head of the first syringe to ready it for administration of the mixed medicament. This system provides improved separation of the components, and can readily be adapted to provide different quantities and proportions of the components, but has a very great overall length (see FIG. 1) and requires a fair amount of manipulation to ready it for use. In common with a number of other systems discussed, the interior volume of the system is substantially increased by the space which must be allowed for displacement of one of the components past a valve or seal without setting up back pressures which will prevent proper operation.

U.S. Pat. No. 4,166,240 (Guiney) discloses an arrangement in which one component of the medicament is stored in a compartment in the plunger of the syringe, from which it may be released in various ways to ready the syringe for use. Clearly the size of the compartment is restricted, and again it is not clear that a positive seal is provided between the compartments.

U.S. Pat. No. 3,659,769 (Schwartz), already mentioned above, differs from other patents in its group in that, rather than being formed in effect by two concentric syringes, the inner of which is discharged into the outer prior to injecting the contents of the latter, only a single syringe is utilized with a hollow plunger which contains a liquid component drawn into admixture with a powder component into the syringe barrel by a vacuum set up by withdrawal of the plunger from the barrel. This arrangement has the advantage of compactness, but is critically dependent for its functionality upon the proper operation of the plunger head, which provides a non-return valving function. Certain embodiments provide an additional seal between the components during storage, but breakage or removal of this seal is also critically dependent upon maintenance of a proper degree of frictional engagement between the parts. For example, in the FIGS. 1-4 embodiment, breakage of the end 42 depends upon the plunger 30 being rotatable in the piston without the piston rotating in the syringe barrel.

U.S. Pat. No. 4,313,440 (Ashley) shows a further centric syringe arrangement, in which an inner syringe has a needle which penetrates the plunger head of an outer syringe and enters a needle of that outer syringe. This device is intended for a number of special purposes in which different liquids are to be injected into and/or withdrawn from a patient, and is not a mixing syringe in the same sense as the other patents considered.

OBJECT OF THE INVENTION

The present invention seeks to provide a hypodermic syringe system for the administration of two component medicaments in which a liquid component of the system can be positively sealed prior to use from contact with the other component, which can be made compact and simple to manipulate, and which can be readily adapted to different proportions and dosages of the components.

According to the invention, a hypodermic syringe for the administration of a medicament having two components requiring separate storage comprises a barrel having a hypodermic needle or provision therefor at one closed end, a hollow plunger stem movable within the barrel and having an outer end projecting from the other end of the barrel, a capsule defining a sealed collapsible chamber containing a first, liquid component of the medicament and entering within the hollow plunger stem, a plunger head sealingly slidable within the barrel and linked to the plunger stem to separate the latter from a second component of the medicament stored within the barrel beyond the plunger head, hollow needle means at the inner end of the plunger stem between the capsule and the plunger head, means to drive the capsule into the plunger stem towards the plunger head whereby the needle means is caused to pierce both said capsule and said plunger head and place the interior of the capsule in communication with the barrel beyond the plunger head, means to maintain said communication during movement of said plunger out of the barrel, and means operable to terminate such communication prior to subsequent movement of said plunger into the barrel.

With such an arrangement, a liquid component of the medicament can be stored in the sealed capsule within the hollow plunger stem until required for use, and the second component may be stored beneath the plunger head. When the syringe is required for use, the capsule and plunger head are moved towards each other so that the hollow needle means pierces both the plunger head and the capsule, and the plunger stem is partially withdrawn from the barrel, the linked plunger head moving with the stem so that a partial vacuum is induced beyond the plunger such as to draw the liquid component in the capsule into admixture with the component stored beyond the plunger head. The communication between the capsule and the space beyond the plunger head is terminated before the plunger is again moved inwardly to eject the contents of the syringe through a hypodermic needle fitted in communication with the previously closed end of the barrel. This interruption can be achieved by a coupling forming the link between the plunger head and stem and permitting sufficient relative movement therebetween for the hollow needle to be withdrawn through the plunger to a retracted position, or by a non-return valve. The design of such a non-return valve is less critical than in prior art arrangements using such a valve, since it is not relied upon to maintain separation between the components of the medicament but instead merely to prevent backflow into the capsule during ejection of the syringe contents. As a further alternative, the capsule may be constructed to interlock with the needle when driven into the latter so that the needle may be withdrawn through the plunger by removal of the capsule.

Further features of the invention will become apparent from the following description of a preferred embodiment of the invention with reference to the accompanying drawings.

BRIEF DESCRIPTION OF THE DRAWINGS

FIGS. 1a, 1b and 1c are enlarged details showing certain specific parts;

FIGS. 2, 3, 4 and 5 are longitudinal cross-sections through the syringe, illustrating successive stages in its operation;

FIG. 6 is an isometric exploded view of a second embodiment of syringe according to the invention;

FIG. 7 is an enlarged detail showing certain parts of the syringe of FIG. 6;

FIG. 8 is an exploded view illustrating certain parts of a further embodiment of syringe, where these differ from the corresponding parts of previous embodiments;

FIG. 9 is a longitudinal cross-section through a further embodiment of syringe;

FIG. 10 is a detailed view illustrating a stage in the utilization of the syringe of FIG. 9; and FIGS. 11A–F are a series of views, some partly in section, illustrating stages in the assembly of yet a further embodiment of syringe.

DESCRIPTION OF THE PREFERRED EMBODIMENTS

Figure 1:
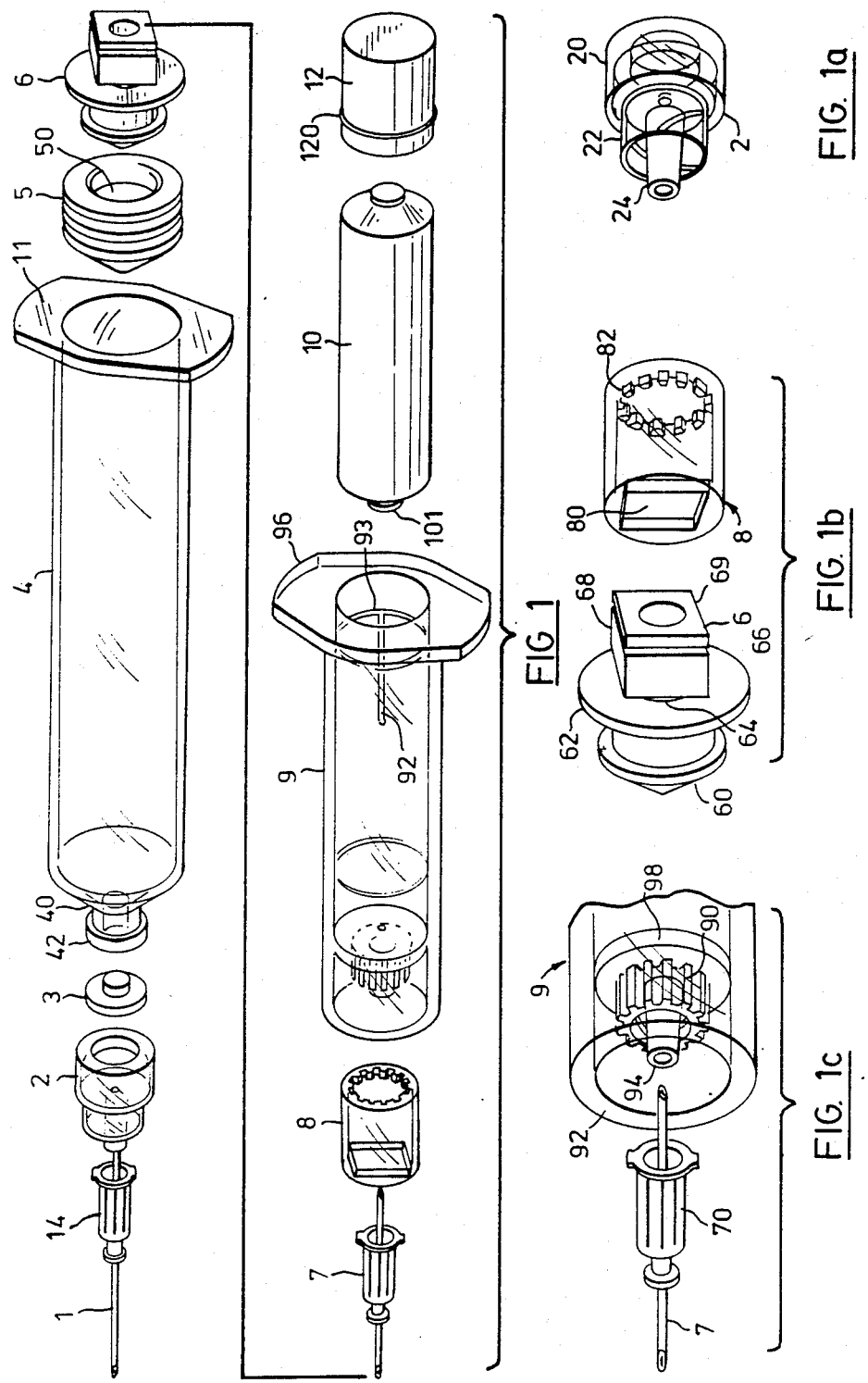
FIG. 1 is an isometric exploded view of a syringe in accordance with one embodiment of the invention, showing its various parts.

The syringe of FIGS. 1–5 comprises a cylindrical syringe barrel which may be of a standard design produced in either glass or synthetic plastic, as desired. The barrel has a neck 40 at one end with a flange 42, providing an opening similar to that found on serum bottles and enabling a first component 44 of the medicament to be dispensed from the syringe to be filled through the neck using equipment designed for filling such bottles. The neck is closed by a rubber stopper 3 of the type used with serum bottles, the rubber being selected, in common with other rubber components of the syringe, to be compatible with the contents of the syringe. The plug is held snugly in place by a moulded plastic cap 2, details of which are best seen in FIG. 1a. The cap has on one end a skirt 20 which is a snap fit over the flange 42, and on the other end a standard locking sleeve 22 and nipple 24 for engagement with a needle, the construction being similar to that of the sleeve and nipple constructions sold under the trade mark LUER-LOK. The needle 1 used with the syringe is of the double ended BC (blood collecting) type, with a straight hollow stainless steel shaft, typically twenty gauge in size, provided with a swaged on flared aluminum hub 14 for engagement with the sleeve 22 and nipple 24. The needle is applied to the syringe only immediately prior to injection, so that the neck 40 of the syringe barrel remains closed by the stopper 3 until the latter is penetrated by the inner end of the needle 1.

Within the barrel 4 is inserted a plunger comprising two main components, a rubber plunger head or piston 5, and a tubular plunger shaft 9. The piston 5 is of rubber and of conventional design, with a free diameter slightly larger than the internal diameter of the barrel 4, so that on insertion it will be slightly compressed to form a hermetic seal with the barrel wall. In a conventional syringe, a re-entrant internal recess 50 in the piston 5 is snapped over an enlarged head on the inner end of the plunger shaft but in the present case connection to the plunger shaft is made through intermediate interlocking components 6 and 8 so as to permit the piston 5 to assume either one of two alternative longitudinal positions relative to the plunger shaft 9. An enlarged head 60 engaging the recess 50 in the piston is formed on a male plunger interlock component 6, the piston being further supported by a flange 62. Rearward of the flange 62, the component has an oblong rectangular cross-section 68, save for two spaced apart grooves 64 and 66 forming necks of reduced circular cross-section. The rear extremity of the rectangular section beyond the groove 66 has a tapered enlargement 69 such that it may be pressed through a complementary rectangular opening 70 in an end of hollow cylindrical female plunger interlock component 8 and be captured therein. The rear of component 8 has internal ribs 82 which lock it securely to ribs 90 formed on the plunger shaft 9. The section 68 of component 6 may thus move longitudinally through the opening 80 between the grooves 64 and 66. When either groove is aligned with the opening 70, the components 6 and 8 may be rotated relative to one another so as to misalign the section 68 with the opening 80, thus locking the two parts in either one of two fixed longitudinal relationships.

The plunger shaft 9 is tubular cylindrical in form, with an outside diameter slightly smaller than the inside diameter of the barrel 4. At an outer open end it is provided with a flange 96 and at its inner end with a sleeve 92 and nipple 94 similar to those at the front end of the barrel 4, so as to interlock with the hub 70 of a further blood collection type needle 7. The needle 7, which preferably has a somewhat larger bore than the needle 1, pierces an inner end wall 98 of the plunger shaft cylinder so as to project into the interior of the latter, while the needle hub 70 is accommodated within the female interlock component 8. The positioning of the grooves 64 and 66 in the male interlock component is such that when the edges of the opening 80 are in a normal position locked within the groove 66, the front end of the needle 7 is housed in a tubular interior of the component 6 (see FIG. 3), while when the edges of the opening engage the groove 64, the front end of the needle pierces the piston 5 (see FIG. 3).

Within the tubular interior of the plunger shaft 9 is housed a capsule 10 containing a liquid component of the medicament to be dispensed. The capsule is moulded from a flexible synthetic plastic or gelatin compatible with its contents, such that its walls are readily collapsible upon draining of its contents, while its end walls, although flexible, have a degree of rigidity with a thicker axial nose 101 which may be pierced by a needle while retaining a fluid seal. Suitable capsules are well known in the art, as are techniques for manufacturing and filling them. The nose 101 of the inner end of the capsule is supported just short of the outer end of the needle 7 by a shallow rib 91 on the inner surface of the tubular shaft 9 such that a pressure on the outer end of the capsule is required to force the inner end of the capsule past the rib, causing the nose 101 to be pierced by the needle 7. A plug 12 is located in the outer end of the tubular shaft such that firm pressure on the plug forces it into the shaft and presses the capsule 10 past the rib 91. The plug is of rubber or plastic with external ridges 120 dimensioned to provide an additional hermetic seal of the syringe contents. However, provision is also made such that when the plug is moved into the tubular shaft from its initial position, air can pass into the shaft as the contents of the capsule are withdrawn as described below. Various methods of achieving this objective are possible. One is to form a groove 95 in the internal wall of the plunger shaft 9 so that, as the rib 120 on the plug 12 is forced forward of a retaining groove 93 in the internal wall, the seal produced by the rib is broken by the groove 92.

The syringe is assembled, shipped and stored in the condition shown in FIG. 2, with the male component 6 in its outward position relative to the component 8 and turned so that the section 68 cannot pass through the opening 80. The needle 1 is not fitted, and may be shipped and stored separately. It will be noted that the syringe is only a little more bulky than a conventional unfilled syringe, and probably less so than a prefilled syringe in that the liquid diluent or carrier is stored in the capsule within the plunger shaft, and only one component of the medicament, usually a soluble powder, need be stored within the barrel. It is also possible to provide interchangeable capsules 10, so as to permit a choice of the quantity or type of diluent or carrier. Capsules may be exchanged simply by removing the plug 12, and shaking out and replacing the capsule.

When the syringe is to be used, the plunger shaft 9 is turned until the opening 80 aligns with the section 68, and the plug 12 is pressed towards the barrel which is gripped by a flange 11 on the barrel 4. This pressure causes the front end of the needle 7 to be forced forward through the plunger head 5 until the component 8 abuts the flange 62 and the opening 80 is thus aligned with the groove 64. The plug 12 forces the capsule 10 forward past the ridge 91 so that its nose 101 is pierced by the rear end of the needle 7, the hollow bore of which forms a communication between the capsule 10 and interior of the barrel 4 in front of the plunger head 5, as shown in FIG. 3.

The plunger shaft 9 is now again rotated so as to misalign the opening 80 and the section 68, and thus lock the component 8 in its forward position relative to component 6, following which the plunger shaft 9 is withdrawn from the barrel 4 as shown in FIG. 5, setting up a partial vacuum ahead of the plunger head 5 which draws the contents of the capsule 10 through the needle 7 into admixture with the component 44. Withdrawal of the shaft 9 continues until either the capsule is fully collapsed, or a desired volume of medicament has been mixed within the barrel 4.

At this point, the plunger shaft is again rotated to align the opening 80 with the section 68, and further withdrawn from the barrel far enough to re-align the opening 80 with the groove 68. This withdraws the needle 7 through the plunger head 5, thus interrupting communication between the capsule 10 and the barrel 4, whereafter the plunger shaft is rotated to lock the needle in its withdrawn position. The needle 1 may then be fitted to the cap 2 causing the rear end of the needle to penetrate the plug 3. The syringe is now ready for use and may be manipulated in conventional manner.

Since the liquid component of the medicament is stored within sealed capsules 10, positive separation of the components during storage is assured. The other component 44 is sealed between the fixed plug 3 and the plunger 5 which is hermetically engaged with the barrel 4. All of the components of the syringe are either standard, readily available syringe components, or readily molded from synthetic plastic or rubber. The syringe and its components may be filled using available equipment. While it is contemplated that the unit described would be disposable, it will be evident that recharging would be possible, although of course a new capsule 10 will be required for each charging, and the rubber components would also desirably be replaced.

Referring now the embodiment of FIGS. 6 and 7, this illustrates a further embodiment of syringe having various features alternative to those of the syringe of FIGS. 1–5.

A different type of needle 1 is shown in which the hub 14 is formed of plastic and is a snap fit on the nipple of an aluminum cap 2 whose skirt is crimped over flange 42, permitting the sleeve 22 to be eliminated. Such needles are readily available, and will not be fitted until the syringe has been prepared for use as described below.

The interlocking component 6 of the first embodiment is replaced by a modified component 6A, and the interlocking component 8 of the first embodiment is replaced by a component 8A integrated into the barrel 9. The component 8A is formed by a forward extension of the barrel 9 having a non-circular, typically oval, cross-section somewhat smaller than that of the barrel, joined to the barrel by a neck 80A of circular cross-section and having a diameter equal to the minor axis of the oval cross-section. The forward end of the extension is closed by a wall having a central orifice into which is screwed the hub 70A of a double ended needle 7A of known type. The component 6A has a hollow cylindrical body with an oval opening 60A at its rear end large enough to admit the component 8A when the major axes of the ovals are aligned, but not otherwise.

FIG. 6 also illustrates an alternative form of capsule 10A, which may be utilized in either embodiment in place of the flexible capsule 10 The capsule 10A is of a known type, having a tubular glass body, having a neck at its forward end closed by a cap 101A including a needle penetrable rubber gasket or plug, in a manner similar to a serum bottle. The glass body defines a collapsible chamber by virtue of a slidable rubber plug 102A forming a hermetic seal with the inside walls of the body as liquid is withdrawn from the latter by a needle inserted through the rubber plug of the cap 101A.

Operation of this embodiment is generally similar to that of the previous embodiment. When the syringe is to be used, the plunger shaft 9 is turned until the major axis of component 8A is aligned with the major axis of the opening 60A, and the plug 12 is pressed towards the barrel which is gripped by the flange 11. The pressure causes the front end of the needle 7 to be forced outward through the plunger head 5 until the rear end of the component 60A abuts the forward end of the shaft 9 adjacent the neck 80A. The plug 12 forces the capsule 10A forward onto the rear end of the needle 7, which penetrates the plug of the cap 101A.

The plunger shaft is now again rotated so that the neck 80A turns in the opening 60A and the major axis of the component 8A is aligned with the minor axis of the opening 60A, thus prevent withdrawal of the component 8A from the opening. The shaft is then withdrawn from the barrel 4, setting up a partial vacuum ahead of the plunger head 5, which displaces the plug 102A and draws the content of the capsule 10A through the needle 7 into admixture with the component 44.

Withdrawal of the shaft 9 continues until either the plug 102A reaches the front end of the capsule, or a desired volume of medicament has been mixed within the barrel 4. At this point, the plunger shaft is again rotated to align the major axis of the component 8A with that of the opening 60A, permitting the component 8A to be withdrawn from the component 6A, whereupon the shaft 9 is once again rotated to prevent re-entry of the component 8A into the component 6A, and may then be used to force the component 6A and the plug 5 forwardly to discharge the contents of the syringe once the needle 1 has been fitted.

In a disposable syringe, the length of the plunger shaft 9 relative to that of the barrel 4 is preferably such that, once the contents of the syringe are fully discharged, any attempt to re-insert the component 8A into the component 6A will result in the flange 96 abutting the flange 11 before the opening 60A can become aligned with the neck 80A. It thus becomes impossible to interlock the components 6A and 8A. This entails that the plunger 5 cannot readily be withdrawn from the barrel, and prevents further use of the syringe. A similar feature may be provided in a conventional disposable syringe not intended for the mixing of two part medicaments, merely by omitting the capsule 10 or 10A, the plug 12, and the needle 7.

Where it is contemplated that the capsules 10 and 10A will be interchangeable, and/or shipped separately, a rubber sheath (not shown) may be placed over that end of the needle 7 projecting into the stem 9 so as to reduce the risk of contamination.

In place of the male and female interlocking components described, other arrangements would be possible. For example, initial pressure on the plug 12 could be arranged to drive the needle 7 forward so as to enter interlocking engagement with the plunger head 5 as well as piercing the latter, and the needle 7 could incorporate a non-return valve to prevent material from passing back through the needle 7 into the capsule 10. With such a valve, no provision would be necessary for withdrawing the needle 7 through the head 5. A simplified arrangement for attaching the needle 1 to the front of the syringe barrel 4, could also be employed, particularly when the entire syringe contents are to be ejected at one time, the only fundamental requirement being that the front end of the syringe barrel be closed during the mixing step. It would also be possible to dispense with the plug 12, and to rely on finger pressure to force the capsule 10 onto the needle 7. In this case, a frangible sealing membrane across the open end of the plunger 9 would be desirable to retain the capsule and help maintain sterility. Alternatively, the capsule could be packed separately.

Since the function of the needle 7 is merely to penetrate the capsule 10 and the plunger head 5 and to provide communication between the capsule and the space in front of the capsule head, it does not necessarily have to be constructed in the manner of conventional hypodermic needles. In the embodiment of FIG. 8, in which components essentially similar to those of previous embodiments carry the same reference numerals as in FIG. 1 and components having similar functions and parts thereof, carry the same reference numerals with the suffix B, a double ended needle 7B is molded integrally out of synthetic plastic material such as polypropylene with a component 8B which in turn is molded integrally with the plunger stem 9. The needle 7B has a central bore, and oppositely projecting tapering needle points 71B and 72B with projecting tapering blades 73B which reinforce the needle and aid penetration.

This embodiment also illustrates an alternative means of coupling between the components 6B and 8B as compared with that illustrated for the components 6A and 8A in the embodiment of FIGS. 6 and 7. The oval opening 60A in the component 6A is replaced by short partial internal threads 61B on opposite sides of a circular opening 60B, and complementary but somewhat longer partial external threads 81B are formed on a circular front end portion 82B of the component 8B, which is otherwise similar to the component 8A in that it is has an oval cross-section and a neck 80B. In preparing the syringe for use, the plunger 9 is turned so that the threads 81B engage the threads 61, allowing the portion 82B to screw forward into the component 6B until the threads disengage and the plunger can move forward, the ovality of the component 8B permitting it to move past the thread portions 61B. When the component 8B is fully inserted in the component 8B, with the needle 7B penetrating the plunger head 5, a fractional turn of the plunger will lock the thread portions 61B into the neck 80B so that the component 61B may be withdrawn with the needle still penetrating the plunger head. A fractional turn of the plunger in the opposite direction will then release the thread portions 61B from the neck 80B so that the component 8B may withdraw the needle from the plunger head, and further fractional turn will pass the threads 61B through the threads 81B and prevent the component 8B from moving back into the component 6B when the plunger stem is moved forward to cause the plunger head 5 to expel the contents of the syringe.

The capsule need not be housed wholly within the syringe body. The embodiments of the invention shown in FIGS. 9 and 10 and FIGS. 11A–F make use of modified versions of accordion style squeeze capsules of a general type manufactured by Automated Liquid Packaging Inc. and sold under the trade mark ALP.

In FIG. 9, the hollow plunger stem 9C of the syringe is connected directly to the plunger head 5, and the plunger stem lacks a flange at its outer end so that it may enter fully within the syringe barrel 4. It has an internally threaded axial opening 97C at its outer end and a further axial opening at its inner end beneath the head 5. The capsule 10C has an accordion pleated cylindrical body of an overall diameter greater than the internal diameter of the syringe barrel 4, and a forward portion 101C of reduced diameter which can enter the syringe barrel. The forward portion has an extension forming a component 8C of still further reduced diameter and formed with two axially spaced externally threaded portion 80C and 81C, the threads of which are complementary to those of the opening 97C. The front end of the component 8C is closed by a diaphragm 83C, in front of which a collapsible collar 84C supports the hub 70C of a doubled ended needle 7C.

In use, one component, usually solid, of a medicament, is stored in the syringe barrel 4 in front of the plunger head 5, as in previous embodiments. The forward part of capsule 10C is first inserted in the plunger barrel and turned so as to engage the threaded portion 81C with the threaded opening 97C (if not shipped in that position). Further turning of the capsule allows the component 8C to be moved forward in the plunger 9C until the needle 7C moving forward through the opening 98C penetrates the plunger head 5, at which point the capsule can be turned further to engage the threaded portion 80C with the threaded opening 97C. Forward movement of the needle 7C is limited by abutment of an enlarged portion of the hub 70C with the edges of the opening 98C, with the result that the collar 84C collapses, causing the rear end of needle 7C to penetrate the diaphragm 83C, thus placing the interior of the capsule in communication with the space forward of the plunger head 5. The capsule 10C itself may then be used to withdraw the plunger stem 9C while collapsing the capsule to discharge its contents through the needle 7C into admixture with the other component of the medicament stored beneath the plunger head 5. Thereafter, the capsule may be rotated to release the threaded portion 80C from the opening 97C and reengage the threaded portion 81C with the opening 97C, at which point the syringe is ready for use after fitting of the needle 1.

One important application of syringes in accordance with the invention is in conjunction with syringe infusers, which provide for gradual discharge of the contents of a syringe into the bloodstream of a patient at a controlled rate over a period of time. An example of such an infuser is the Harvard syringe infuser sold by Bard, in which a syringe, connected to an intravenous needle in a patient by a flexible narrow bore tube fitted over the syringe needle is placed in a holder and gradually discharged by a motorized plunger acting on the syringe plunger. To adapt the syringe of FIG. 9 for use in such a system, the capsule 10C, after discharge of its contents, is maintained in a collapsed state as shown in FIG. 10 by means of a collar 103C slipped over the concertina folds of the collapsed capsule, thus converting it into a substantially rigid extension of the plunger 9C.

A disadvantage of the embodiment of FIGS. 9 and 10 is that it requires the needle 7C to be incorporated into the structure of the capsule 10C, which requires special equipment, and increases the cost of the capsule. The problem is overcome in the embodiment whose assembly is illustrated by FIGS. 11A–11F. In this embodiment, the tubular plunger stem 9D may be of more conventional form with a flange 96D at its outer end, and the hub 70D of needle 7D is provided with an enlarged flange 75D which cannot pass an aperture 98D in the front end of the plunger. The capsule 10D is generally similar to the capsule 10C, except that its forward portion 101D is elongated so as to be able to extend the full depth of the plunger 9D. The collapsible collar 84D at the front of the capsule forwardly of the diaphragm 83D has an entry ring 85D which is capable of detenting engagement with a rib 76D on the needle hub 70D.

To assembly the syringe, the plunger 9D is turned front end uppermost (see FIG. 11A), the needle 7D is dropped into the aperture 98D so that the flange 75D rests in a bore surrounding the aperture (FIG. 11B), and the plunger head 5 is engaged with the front end of the plunger 9D (FIG. 11C) thus trapping the needle assembly. The assembled plunger is then inserted in the syringe barrel 4 (FIG. 11D) leaving a space at the top sufficient to contain the solid component 44 of a medicament to be dispensed from the syringe. The solid component is dispensed into this space, a stopper 2 and a cap 1 are applied using conventional powder filling and capping machinery, parts of a star wheel forming part of such machinery being shown in broken lines in FIG. 11E. The capsule 10D is then inserted in the plunger as shown in FIG. 11F, or the capsule may be shipped separately.

In use, the capsule 10D is pressed forward into the plunger 9D so that the rear end of needle 7D penetrates the diaphragm 83D and the rib 76D is forced through the entry ring 85D of the collar 84D, whilst the other end of the needle 7D is forced through the plunger head 5. The plunger 9D is then withdrawn whilst pressing on the capsule so as to eject the contents of the latter through the needle 7D into admixture with the component 44 above the plunger head 5. The capsule 11D is then pulled out of the plunger. Because of the detenting engagement between the rib 76D and the ring 85D, the needle 7D is pulled rearwardly out of the plunger head until the flange 75D again engages the sides of aperture 98D, thus halting the needle and pulling the flange 76D out of engagement with the ring 85D. Removal of the capsule leaves the syringe ready for use after fitting of a needle.

If the capsule 10D were made of larger capacity, and provided with a self sealing diaphragm 83D, it would be possible to utilize a single capsule of diluent to suspend or dissolve the solid component of a number of syringe assemblies.

I claim:

1. A syringe for the administration of a medicament having two components requiring separate storage comprises: a barrel having a neck at one end, a penetrable closure for said neck, means mounted on said neck for receiving a double ended needle with one end thereof in penetrating relationship with said closure, a hollow plunger stem movable with the barrel, a capsule defining a sealed collapsible chamber comprising a first, liquid component of the medicament and entering within the hollow plunger stem, a plunger head sealingly slidable within the barrel to isolate a second component of the medicament stored within the barrel beyond the plunger head, means coupling the plunger head and the plunger stem, hollow needle means located at the inner end of the plunger stem between the capsule and the plunger head, and means to drive the capsule towards the plunger head whereby the needle means is caused to pierce said capsule and place the interior of the capsule in communication with the hollow needle means, the coupling means comprising two relatively axially movable parts having twist coupling means such that they are capable of assuming two alternative axially spaced relative positions, in each of which they can be retained against relative axial movement in at least one direction, the longitudinal position of the plunger head relative to the needle in a first of the positions, in which the parts can be retained against movement toward one another, being such that the needle does not pierce the head, and in a second of the positions, in which the parts can be retained against movement away from each other, being such that the needle does pierce the head;

wherein the first of said axially movable parts is a sleeve attached to one of the head and the plunger stem, and the second of said parts is a hollow stem attached to the other of the head and the plunger stem and telescopically entering the sleeve, the sleeve having an axially asymmetric opening, and the stem having an asymmetric section having at least one orientation in which it can move axially into said opening, and at least one neck permitting the opening in the sleeve to be rotated out of said at least one orientation in at least the second of said axially spaced positions.

2. A syringe according to claim 1, wherein the stem has a second neck permitting the opening in the sleeve to be rotated out of said at least one orientation in the first of said axially spaced positions.

3. A syringe according to claim 1, wherein in the first of said axially spaced positions, the axially slidable parts are in axial abutment and are freely movable away from each other.

4. A syringe according to claim 3, wherein the plunger stem has a flange limiting the length of the stem insertable in the barrel, this length being such that, when the plunger head is fully inserted in the barrel, the axially slidable parts cannot attain the second of said axially spaced positions.

5. A syringe according to claim 1, wherein said hollow stem has an internal means normally supporting said capsule out of contact with said hollow needle means.

6. A syringe according to claim 1, further including a plug at the external end of the plunger stem slidable into the stem at a position pressing the capsule onto said hollow needle means.

7. A syringe according to claim 6, including means to vent air past said plug when in a position pressing said capsule onto said hollow needle means.

8. A syringe according to claim 1, wherein said hollow needle means is a double ended needle.

9. A syringe according to claim 1, wherein the closed end of the syringe has a neck closed by a rubber plug and a cap for receiving a double ended needle.

10. A syringe according to claim 1, wherein the capsule is a flexible collapsible capsule.

11. A syringe according to claim 1, wherein the capsule is a rigid tubular capsule, with a plug slidable therein to define said collapsible chamber.

12. A syringe according to claim 1, wherein one of said relatively axially slidable parts is moulded integrally with said plunger stem from synthetic plastics material.

13. A syringe according to claim 1, wherein the hollow needle means is also moulded integrally with said plunger stem.

14. A syringe for the administration of a medicament having two components requiring separate storage comprises a barrel having a neck at one end, a penetrable closure for said neck, means mounted on said neck for receiving a double ended needle with one end thereof in penetrating relationship with said closure, a hollow plunger stem movable within the barrel, a capsule defining a sealed collapsible chamber comprising a first, liquid component of the medicament and entering within the hollow plunger stem, a plunger head sealingly slidable within the barrel to isolate a second component of the medicament stored within the barrel beyond the plunger head, means coupling the plunger head and the plunger stem, hollow needle means located at the inner end of the plunger stem between the capsule and the plunger head, and means to drive the capsule towards the plunger head whereby the needle means is caused to pierce said capsule and place the interior of the capsule in communication with the follow needle means, the coupling means comprising two relatively axially movable parts having twist coupling means such that they are capable of assuming two alternative axially spaced relative positions, in each of which they can be retained against relative axial movement in at least one direction, the longitudinal position of the plunder head relative to the needle in a first of the positions, in which the parts can be retained against movement toward one another, being such that the needle does not pierce the head, and in a second of the positions, in which the parts can be retained against movement away from each other, being such that the needle does pierce the head;

wherein one of said relatively axially moveable parts has an axially short threaded portion, and the other of said relatively axially moveable parts has two axially spaced portions for alternative rotational engagement with said threaded portion in said respective axially spaced relationships, and a portion intermediate said axially spaced portions which can move freely through said threaded portion.

15. A syringe according to claim 14, wherein at least one of said axially spaced portions is formed with threads complementary to those of the threaded portion.

* * * * *